(12) United States Patent
Ellman et al.

(10) Patent No.: US 6,712,813 B2
(45) Date of Patent: Mar. 30, 2004

(54) RF PROBE FOR ELECTROSURGICAL INSTRUMENT

(76) Inventors: Alan G. Ellman, 1135 Railroad Ave., Hewlett, NY (US) 11557; Jon C. Garito, 1135 Railroad Ave., Hewlett, NY (US) 11557

( * ) Notice: Subject to any disclaimer, the term of this patent is extended or adjusted under 35 U.S.C. 154(b) by 0 days.

(21) Appl. No.: 09/962,025

(22) Filed: Sep. 26, 2001

(65) Prior Publication Data

US 2003/0050634 A1 Mar. 13, 2003

Related U.S. Application Data

(63) Continuation-in-part of application No. 09/950,611, filed on Sep. 13, 2001.

(51) Int. Cl.[7] ............................................. A61B 18/14
(52) U.S. Cl. ............................. 606/41; 606/45; 606/49
(58) Field of Search ....................... 606/41, 42, 45, 606/48, 49, 50

(56) References Cited

U.S. PATENT DOCUMENTS

| | | | | | |
|---|---|---|---|---|---|
| 1,943,543 A | * | 1/1934 | McFadden | ................ | 606/49 |
| 1,983,669 A | * | 12/1934 | Kimble | ................ | 606/50 |
| 3,825,004 A | * | 7/1974 | Durden, III | ................ | 606/49 |
| 4,071,028 A | * | 1/1978 | Perkins | ................ | 606/37 |
| 4,476,862 A | * | 10/1984 | Pao | ................ | 606/50 |
| 4,517,975 A | * | 5/1985 | Garito et al. | ................ | 606/41 |
| 4,548,207 A | * | 10/1985 | Reimels | ................ | 606/50 |
| 5,342,356 A | * | 8/1994 | Ellman et al. | ................ | 606/42 |
| 5,374,188 A | * | 12/1994 | Frank et al. | ................ | 606/49 |
| 5,733,282 A | * | 3/1998 | Ellman et al. | ................ | 606/45 |
| 5,807,392 A | * | 9/1998 | Eggers | ................ | 606/29 |
| 6,312,428 B1 | * | 11/2001 | Eggers et al. | ................ | 606/41 |

* cited by examiner

Primary Examiner—Lee Cohen (57) ABSTRACT

An electrosurgical handpiece having a removable section permanently incorporating an electrode adapted for a particular procedure. The handpiece may be labeled for that procedure or otherwise visually distinguished from other handpieces, as, for example, by shape or color-coding, and the optimum electrode for that procedure is already pre-attached to the handpiece. The handpiece comprises a common connector attached at one end to a cable terminating in an end connector for attachment to an electrosurgical instrument, and at its other end adapted to receive and hold and electrically connect to the handpiece proper itself, i.e., a handle for the surgeon to hold and the attached electrode. A family of handpieces are preferably configured to removably attach to the common connector and thus could use the same common connector and cable and end connector for connecting to the instrument as a source of RF electrosurgical currents. The shape of the handpiece can also be related to the orientation of the electrode so that the surgeon can tell by the position of the handpiece in his hand the position of the electrode at the patient's tissue.

11 Claims, 5 Drawing Sheets

RF PROBE FOR ELECTROSURGICAL INSTRUMENT

RELATED APPLICATION

This invention is A CONTINUATION-IN-PART of a commonly owned patent application, Ser. No. 09/950,611, filed in the U.S. Patent And Trademark office on Sep. 13, 2001 and entitled INTELLIGENT SELECTION SYSTEM FOR ELECTROSURGICAL INSTRUMENT.

This invention is directed to a radio-frequency (RF) probe or handpiece for use with and for controlling an electrosurgical instrument or apparatus.

BACKGROUND OF INVENTION

Electrosurgical instruments are well known and widely used in the medical, dental, and veterinarian fields. They offer the capability of precision cutting and coagulation with electrosurgical currents preferably in the megacycle range using a handpiece with, for example, removable needle, ball, or loop electrodes in a unipolar operating mode or with a forceps in a bipolar operating mode. Ellman International, Inc. makes available an electrosurgical instrument for Radiosurgery which provides on its front panel connectors for receiving the plug of a cable-connected unipolar handpiece and a ground or indifferent plate, as well as connectors for receiving the plug of a cable-connected bipolar electrode. One form of such an instrument is described in U.S. Pat. No. 5,954,686, whose contents are incorporated herein by reference. Such instruments are characterized by different modes and sub-modes of operation. For example, the instrument described in the patent, which is typical of other similar instruments, has a cutting mode, separable into CUT and CUT/COAG sub-modes, and a coagulation mode, separable into HEMO, FULGURATE, and BIPOLAR sub-modes.

In a typical surgical setting using such an instrument, a surgeon may first use a handpiece while the instrument is in its cutting mode to perform a desired cutting procedure and then desire to use the same handpiece for coagulation of blood vessels while the instrument is in its coagulation mode. To this end, the electrosurgical instrument has on its front panel push buttons or switches for activating internal circuitry for switching the electrosurgical instrument from its cutting to its coagulation mode or vice-versa. A current electrosurgical instrument contains a power-supply-controlled radio-frequency (RF) oscillator which generates RF currents typically in the megacycle range as high-frequency AC waves. For most cutting purposes, the AC waveform is fully filtered to produce an approximate DC waveform. For most coagulation purposes, the AC waveform is partially rectified (commonly half-wave rectification) to produce the characteristic half-wave rectified waveform. This is accomplished by switching in certain rectifier and filter components for the cutting mode, and switching in certain rectifier components for the coagulation mode. This is well known in the art and further description is unnecessary. Suffice to say, the switching action occurs inside the instrument when the front panel controls are activated by the surgeon.

To simplify mode selection by the surgeon, it is known to place on the handpiece two finger-activated switches that can be connected by appropriate wiring to the electrosurgical instrument and wired in parallel with the front panel switches so that activation of either the finger switches on the handpiece or the front panel switches will allow mode selection. This is similar to the connection and operation of a foot switch that can be used by the surgeon to activate and deactivate the RF currents. More modern electrosurgical instruments, however, do not lend themselves to such a simple approach. The typical modem electrosurgical instrument is computer-controlled, typically by a microcontroller ($\mu$C); hence simple parallel-connected circuitry may not work satisfactorily. Another problem is that the standard handpiece has only three terminals, one of which is dedicated to carrying the high-frequency or RF electrosurgical currents; hence, mode selection must be carried out in a safe manner using only two of the three terminals.

A further complication in the use of such instruments is the variety of surgical procedures to which the instrument can be applied, often with different electrodes. Each surgical procedure typically requires not only a particular electrosurgical mode, such as cut or cut/coag, or hemo, but also may require a different set of mode conditions, such as the power setting and/or a different time duration of power application. Each typically requires a different electrode. The Ellman company, as an example, offers between 50 and 100 different electrodes including shapes and sizes for the various medical specialties.

With four therapeutic waveforms available in current Radiosurgery instruments and a wide power range, it is time consuming and memory dependent on the part of the surgeon and or staff to choose and mount in the handpiece an electrode for the desired procedure, and then tune in the correct waveform and power settings for the particular procedure to be carried out. Also there may have been occasions when electrosurgical injuries or increased recovery times may have occurred due to the choice of the electrode used as well as incorrect waveform settings and incorrect power settings for the chosen procedure.

SUMMARY OF INVENTION

A principal object of the invention is a handpiece for an electrosurgical instrument for use by the surgeon whose choice depends primarily on the surgical procedure to be employed.

Another object of the invention is a handpiece for an electrosurgical instrument that eliminates or reduces the chance of the surgeon choosing the incorrect or less than optimum electrode for the surgical procedure to be employed.

A further object of the invention is a handpiece in which the choice of the handpiece controls the operating mode of the instrument, preferably, also the mode conditions, that is desired for carrying out a particular procedure.

These objects are achieved in accordance with one aspect of the invention by a novel handpiece construction comprising an electrode that is permanently attached or mounted to the handpiece. In a preferred embodiment, the surgeon has available a family of such handpieces each configured and adapted for either the same procedure, as for example different shapes or sizes of electrodes, or for a different procedure in the surgeon's specialty. So, for example, if procedure A is to be carried out, then handpiece A is selected which includes the electrode that the surgeon deems best for that procedure. Similarly, if procedure B is to be carried out, then handpiece B is selected which includes the electrode that the surgeon deems best for procedure B. Fewer electrode errors are possible, in another preferred embodiment, because the handpiece may be labeled for that procedure or otherwise visually distinguishable from other handpieces, as, for example, by shape or color-coding, and the optimum electrode for that procedure is already pre-attached to the handpiece. While this arrangement seems to imply greater cost, as multiple handpieces are required to cover all the procedures that the surgeon typically performs, the cost to manufacture each handpiece is far below that of the standard handpiece and so the overall cost may not be significantly greater, keeping in mind the comfort of knowing that errors are less likely to occur.

In a further preferred embodiment of the invention, to further reduce costs, the handpiece comprises a common connector attached at one end to a cable terminating in an instrument end connector for attachment to the instrument, and at its other end adapted to receive and hold and electrically connect to the handpiece proper itself, meaning a handle for the surgeon to hold and the attached electrode. Each member of the family of handpieces are preferably configured to removably attach to the common connector and thus could use the same common connector and cable and end connector for connecting to the instrument as the source of RF electrosurgical currents. As a result, the user need purchase only one common connector/cable accessory usable with any of the handpiece family members.

For convenience of explanation, "handpiece section" as used herein shall mean the removable handles each holding an electrode, "cable-connector section" shall mean the common connector for the handles, attached cable, and end connector for the instrument, and "handpiece" or "probe" shall mean the combination of the two sections making up a working unit.

In the copending referenced application (PAT112), whose contents are herein incorporated by reference, dedicated handpieces are described that incorporate a electrical component, such as an impedance (resistor, capacitor, inductor, transistor or IC), a microprocessor or microcontroller, or storage means such that the handpiece generates a unique control signal that when processed by a microprocessor or microcontroller in the electrosurgical instrument will automatically select that particular set of mode conditions specific to the procedure to which the handpiece is dedicated, the mode conditions including a desired RF current mode as well as operating conditions such as power. The handpieces of this invention are uniquely suited to incorporate the invention of the copending application as each handpiece here already has an electrode pre-attached so it is only necessary to incorporate in the handpiece the appropriate electrical component to implement the invention of the copending application when it is combined with an electrosurgical instrument containing the means to interpret and implement the dedicated handpiece concept.

As a further feature of the invention, the appearance of the handpiece is controlled, as for example, by color-coding or by its shape, so that the surgeon understands that a specific colored or shaped handpiece is associated with a specific procedure, which will further minimize the possibility of surgeon error. As an additional feature, the shape of the handpiece can be related to the position of the electrode so that the surgeon can tell by the position of the handpiece in his hand the orientation of the electrode at the patient's tissue.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention, like reference numerals or letters signifying the same or similar components.

DETAILED DESCRIPTION OF PREFERRED EMBODIMENTS

Figures 1, 2:
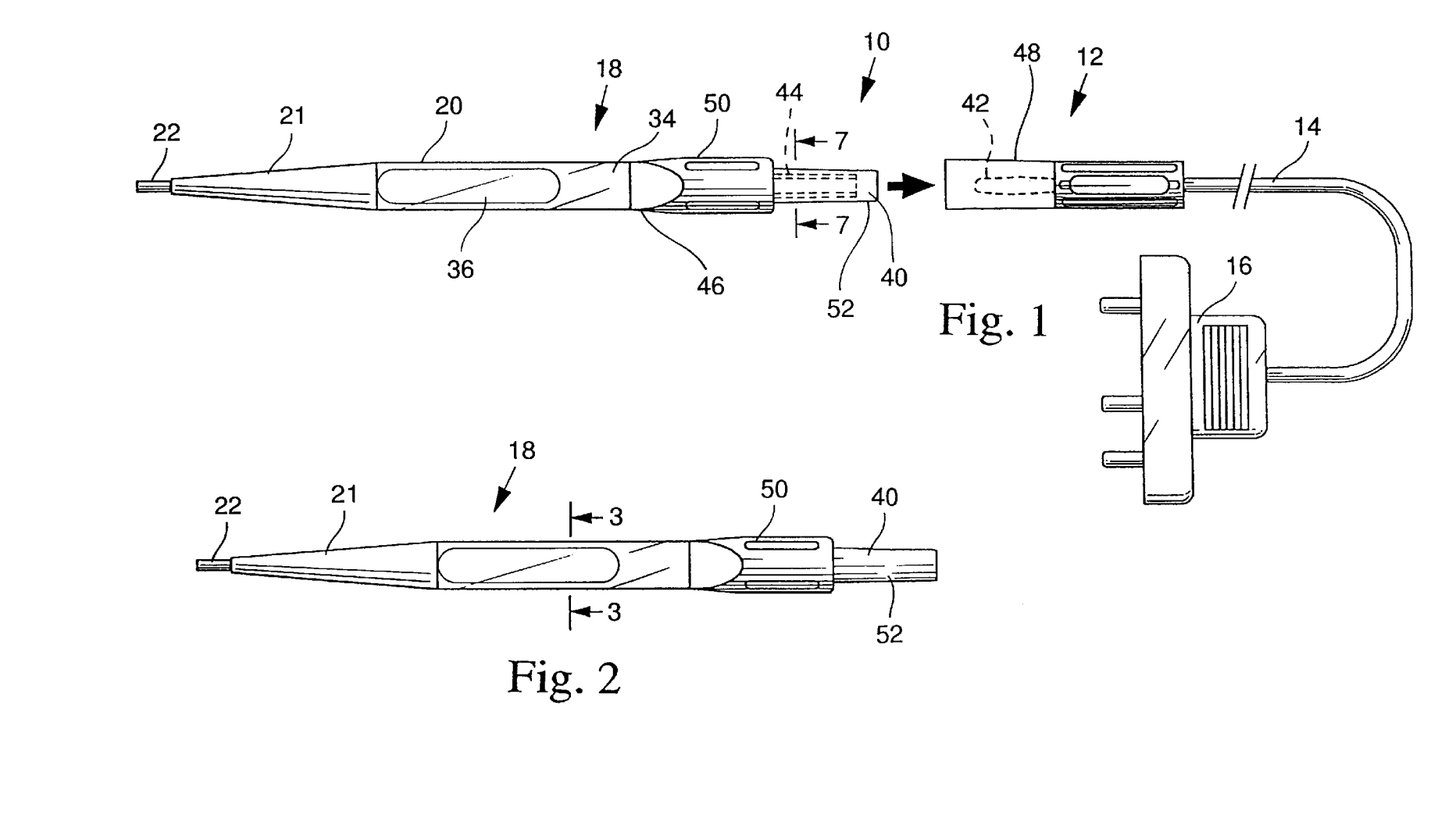
FIG. 1 is a top view of one side of one form of electrosurgical handpiece in accordance with the invention.
FIG. 2 is a top view of another side of just the handpiece section of the handpiece of FIG. 1.

One form of an electrosurgical handpiece 10 according to the invention is illustrated in FIG. 1. It comprises on the right a cable connector section 12 comprising an electrical cable 14 terminating in a standard connector 16 for plugging into the complementary connectors of an electrosurgical instrument or system unit (not shown) which typically comprises a box-like housing with a front control panel for the instrument. The control panel may include touch switches for selecting cutting or coagulation modes and touch switches for controlling the power output by increasing or decreasing in steps the power, which would be indicated by digital displays on the front panel. At the bottom are typically output female connectors for receiving a unipolar handpiece, a bipolar handpiece or forceps, and a neutral plate. An on-off power switch is also present. The instrument may be of the type described in connection with the control unit of U.S. Pat. Nos. 4,463,759 and 5,954,686, whose contents are herein incorporated by reference, which circuitry is in this case incorporated in the system unit. A connector is also typically provided at the side for receiving a conventional footswitch. In use, for example, if the surgeon determines that s/he is going to perform a cutting or coagulation procedure with a particular electrode, then s/he can set the cutting mode power on the control panel. (Typically, these units are designed to supply up to 100 watts of RF power to either handpiece.) Upon pressing the footswitch, RF electrosurgical currents are transmitted along the cable to the handpiece held in the surgeon's hand. The RF electrosurgical currents are appropriately modulated to generate different output waveforms used for the known CUT, CUT/COAG, HEMO, and FULGURATE modes. These typically are: CUT-CW (full-wave rectified and filtered) output with maximum average power; CUT/COAG-full-wave rectified but unfiltered, deeply modulated, at 37.5 or 75 Hz rate, envelope with approximately 70% average to peak power ratio; HEMO-half-wave rectified and unfiltered, deeply modulated, at 37.5 or 75 Hz rate, envelope with approximately 35% average to peak power ratio; FULGURATE (or Spark-Gap Wave)-deeply modulated, 3.6 KPPS random rate with approximately 20% average to peak power ratio. The circuitry to generate these waveforms are well known in the art and are not a part of this invention. Suffice to say that the particular procedure to be carried out often requires particular RF electrosurgical currents and a particular electrode shaped or sized for that procedure. More details can be found in the referenced copending application.

In the typical prior art handpiece, the different electrodes have standard sized shanks so that they can all be fitted in the collet end of the handpiece. When a different electrode is needed, the surgeon or his or her assistant loosens the collet, removes the previous electrode, inserts a new electrode, and tightens the collet.

The present invention is characterized by handpieces that incorporate fixed electrodes that are not removable. In addition, the handpiece is constructed in two parts; a first removable handpiece section and a second cable connector section, with a family of handpiece sections having similar coupling sections allowing each of them to be connected to the cable connector section as desired. In other words, it is not the electrode that is removable and interchangeable with other electrodes as in the prior art that we are aware of, but rather the handpiece section that is removable and interchangeable with other handpiece sections in accordance with the invention.

Figures 14, 15:
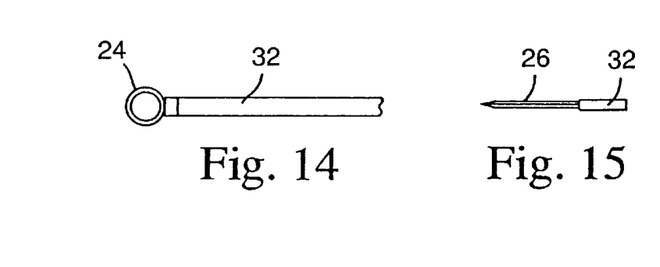
FIGS. 14, 15, 16, and 17 are elevational views of different typical forms of electrodes that can be attached to the handpiece of the invention.
Figure 16:
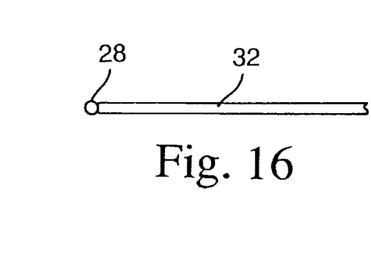
Figure 17:
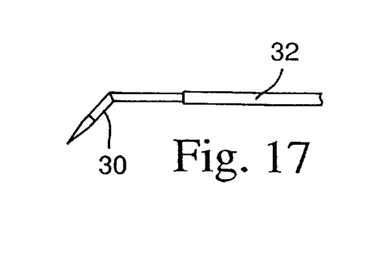

Referring now back to the drawings, a handpiece section 18 is adapted to be fitted to and mounted to the cable-connector section 12. The handpiece section 18 comprises a handle part 20 which tapers 21 toward a front end into which is permanently mounted an electrode 22 which can be any of the well known sizes and shapes of electrosurgical electrodes. Some examples are given, for example: electrode 22 in FIG. 1 is a side view of a wire or rod, and it would also be a side view of a circular curette or ring (the curette 22 is also shown from the top in FIG. 10); a blade or disc 24 with a sharpened periphery shown in FIG. 14 (see U.S. application Ser. No. 09/819,017, whose contents are incorporated, for further details); a larger sized disc 26 shown in FIG. 15; a ball 28 shown in FIG. 16; an angled wire electrode with a sharpened point 30 shown in FIG. 17. As will be noted, the electrode can be provided with a shorter or longer shank 32 depending upon the procedure. When a curette is the electrode, it is preferred that the sharp edge faces downward and the blunt side faces upward.

Figure 3:
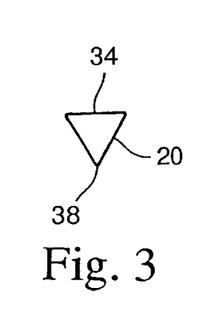
FIG. 3 is a view along the lines 3-3 showing the outer triangular shape of the handpiece section of FIG. 2.
Figure 4:
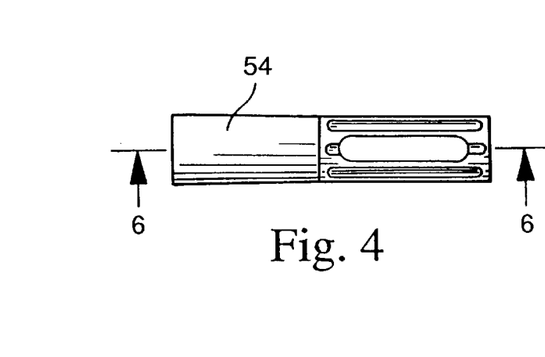
FIG. 4 is a top view of the common connector of the cable connector section shown without the cable of the handpiece of FIG. 1.
Figure 7:
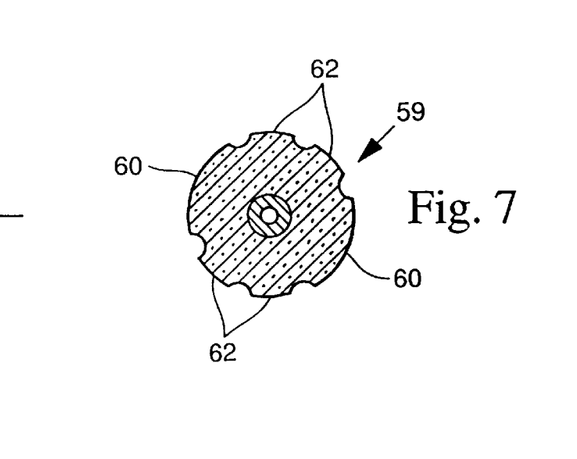
FIG. 7 is a cross-sectional view of the widened part of the handpiece section of FIG. 1, also representing the section along the line 7-7 of FIG. 10.

The handle 20 has a triangular shape, as shown in FIG. 3. Preferably, one of the handle sides is distinguished by feel or visibly, such as by a bump or by a different color from the other sides so that the surgeon will know the exact orientation of the electrode with respect to that one side. So in the example of FIG. 1, by providing the top side 34 with a distinguishing color 36, and assuming that the electrode is not circular symmetrical but has a significant orientation, such as if the electrode 22 were a ring, or the disc 24 of FIG. 14, and the plane of the electrode 22 is aligned with the bottom vertex 38, the surgeon knows by the position of the triangular handle 20 in his hand the orientation of the electrode 22. Other handle shapes, such as polygonal, and electrode orientations are also within the invention. For example, the plane of the electrode may be aligned with a flat side of the handle or with a longitudinal ridge running along one side of a round handle or with a longitudinal section of the handle that is differently colored. In other words, any structure or color that makes the handle non-circular symmetric can be used to inform the surgeon of the handle position in his hand relative to a particular electrode that is also non-circular symmetric. In the embodiment illustrated by the cross-section of FIG. 7, it will be noted that the widened end 59 of the body has two wide arcs 60 on opposite sides and four smaller arcs 62 between. As a result, the user using the widened end 59 can still determine electrode orientation by his hand grip on the handle.

Figure 5:
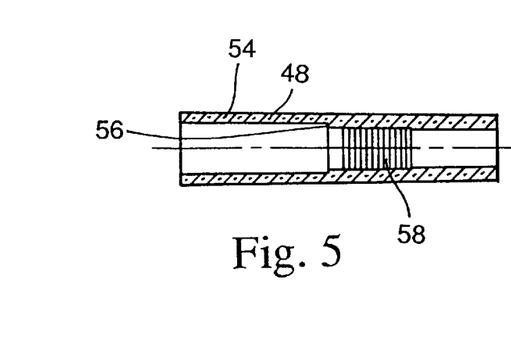
FIG. 5 is a longitudinal cross-sectional view of just the electrically-insulating part of the cable connector section of FIG. 4.
Figure 6:
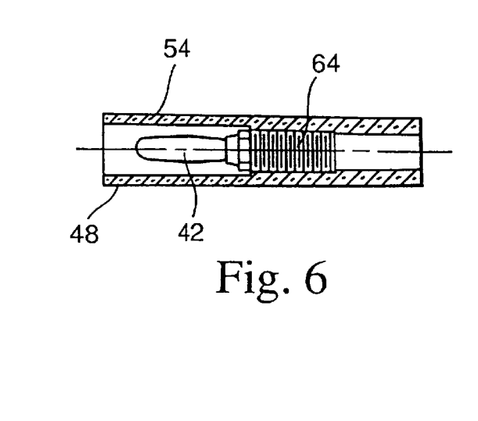
FIG. 6 is a longitudinal cross-sectional view along the line 6-6 of the cable connector section of FIG. 4.
Figure 8:
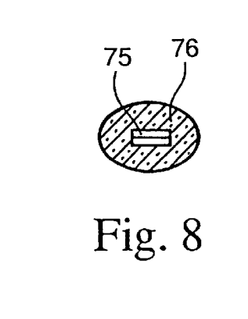
FIG. 8 is a cross-sectional view of the tapered part of the handpiece section of FIG. 1, also representing the section along the line 8-8 of FIG. 11.
Figure 9:
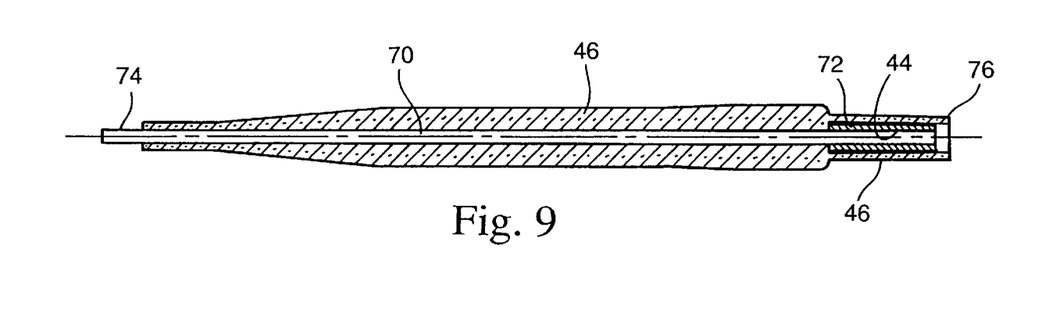
FIG. 9 is a longitudinal cross-sectional view along the line 9-9 of the handpiece section shown in FIG. 11.
Figure 12:
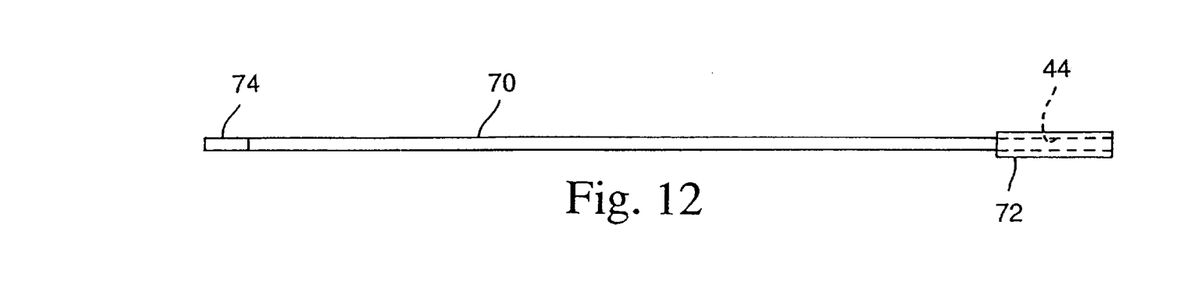
FIG. 12 is an elevational side view of one form of the internal electrically-conducting tube of the handpiece section in accordance with the invention shown with an attached electrode.

Returning now to FIG. 1, on its right side the handpiece section 18 has an end portion 40 configured to engage for mounting and to electrically connect to the cable-connector section 12. Various shapes and structures are suitable for this purpose. A preferred construction uses a recessed male connector 42 engaging a suitably-sized recessed cylindrical female connector 44 when the two sections are engaged. The recessing of the male 42 and female 44 connectors within, respectively, a high-pressure molded electrically-insulating sheath 46 on the handpiece section and a similar molded body 48 on the cable-connector section, for example, of high-impact nylon or similar plastic, is an important safety feature to avoid personnel accidentally touching a live electrical part during the procedure. Thus, it becomes possible with complete safety for the surgeon or his assistant to switch the handpiece section 18 at any time during the procedure. Preferably, the handpiece section 18 has a widened end 50 followed by a reduced diameter section 52 which is sized for a smooth and snug fit without wobbling within a receiving section 54 at the left end of the cable-connector section (FIG. 6). When the reduced diameter section 52 engages the receiving section 54, a good electrical connection is automatically established between the female conductor 44 and the male conductor 42, which preferably is shaped as a banana plug for better contact. The molded electrically-insulating part 54 is shown alone in FIG. 5, and comprises an internal shoulder 56 and an internal screw thread 58. The banana plug 42 can be obtained with a screw base 64 which can be screwed into the internal thread 58 to secure the plug 42 in place (FIG. 6). The plug 42 has a flange that seats against the shoulder 56. While not shown in FIG. 6, in the assembly process, the bare end of the cable 14 would be soldered or otherwise secured in good electrical contact inside the plug fitting and then the wire from the left side passed through the free end of the section and assembled to the predetermined-molded body 54 until the plug screw encounters the internal thread 58 and the latter screwed together until the plug engages the shoulder 56 to securely mount the plug and cable within the electrically-insulating body 54. Afterwards, the connector 16 can be attached to the opposite cable end. So, in the case of the cable-connector section 12, its body 54 is pre-molded before the banana plug 42 and cable 14 are assembled. In the preferred case of the handpiece section 18, a metal hollow tube 70, for example, of stainless or brass, is provided (FIG. 12). It has a widened hollow end 72 which surrounds the female connector 44. An electrode 74, in this case a metal ring, is crimped hard 75 within the left end of the hollow tube 70 (see the cross-section of FIG. 8) so that a secure connection results, and then a plastic sheath 46 is injection-molded around the tube 70 as shown in FIG. 9. The crimping should be sufficiently hard to prevent the electrode from inadvertently rotating during use. The crimping is preferred as it avoids the use of solder and thus allows a stronger body to be provided by high-temperature injection molding. The entire metal tube 70 is buried within the electrically-insulating sheath 46 except for the bare electrode end 74. Note that the electrically-insulating part 46 extends beyond the right end 72 of the tube. In this case, it is preferred that the end of the body 46 adjacent the electrode 74 be oval shaped to accommodate the wider crimp 75.

Figure 10:
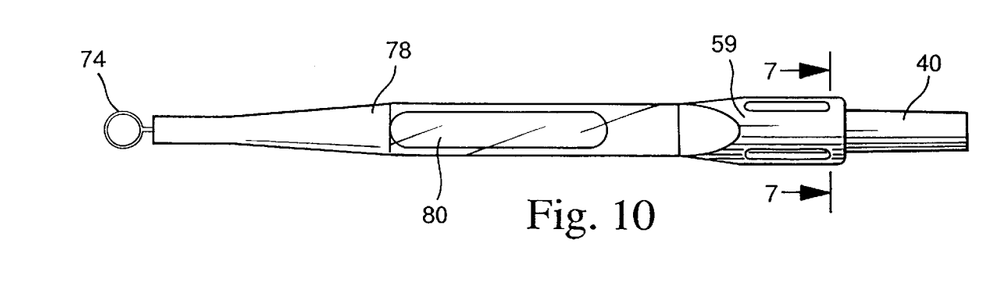
FIG. 10 is an elevational view of one side of another form of handpiece section in accordance with the invention.
Figure 11:
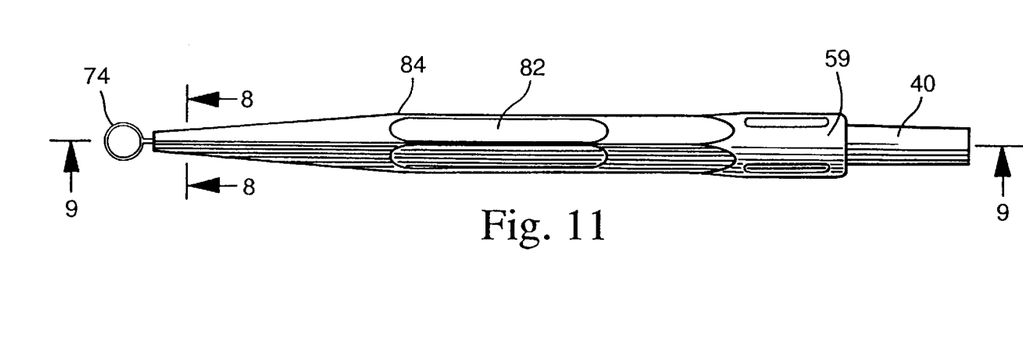
FIG. 11 is an elevational view of another side of the handpiece section of FIG. 10.
Figure 13:
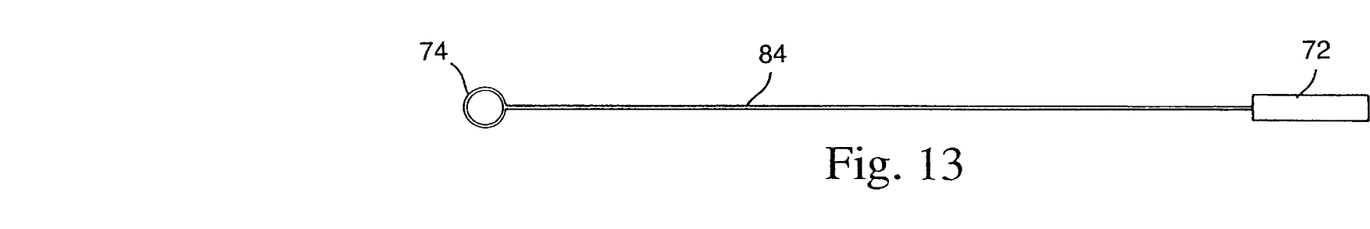
FIG. 13 is an elevational top view of the electrically-conducting tube of FIG. 12.

In the FIG. 10 embodiment, the body 78 shape is generally round with a flat side 80 in the plane of the ring 74. In the FIG. 11 embodiment, the body 82 has a square cross-section with the plane of the ring 74 aligned with one of the vertices 84 of the square. FIG. 13 illustrates a variation 84 of the metal tube which can be oval shaped, except for the widened end 72 which is round to receive the round banana plug 42. It will be evident to those skilled in this art that other ways of providing an electrically-insulating handpiece section surrounding an electrical connector interconnecting the electrode end and the female connector end are readily devised and are also considered within the scope of the invention.

The benefits offered by the novel handpiece construction of the invention are now summarized.

1. A simple unipolar handpiece is achieved that requires no finger switches and is easily operated by the conventional foot pedal control.

Figure 18:
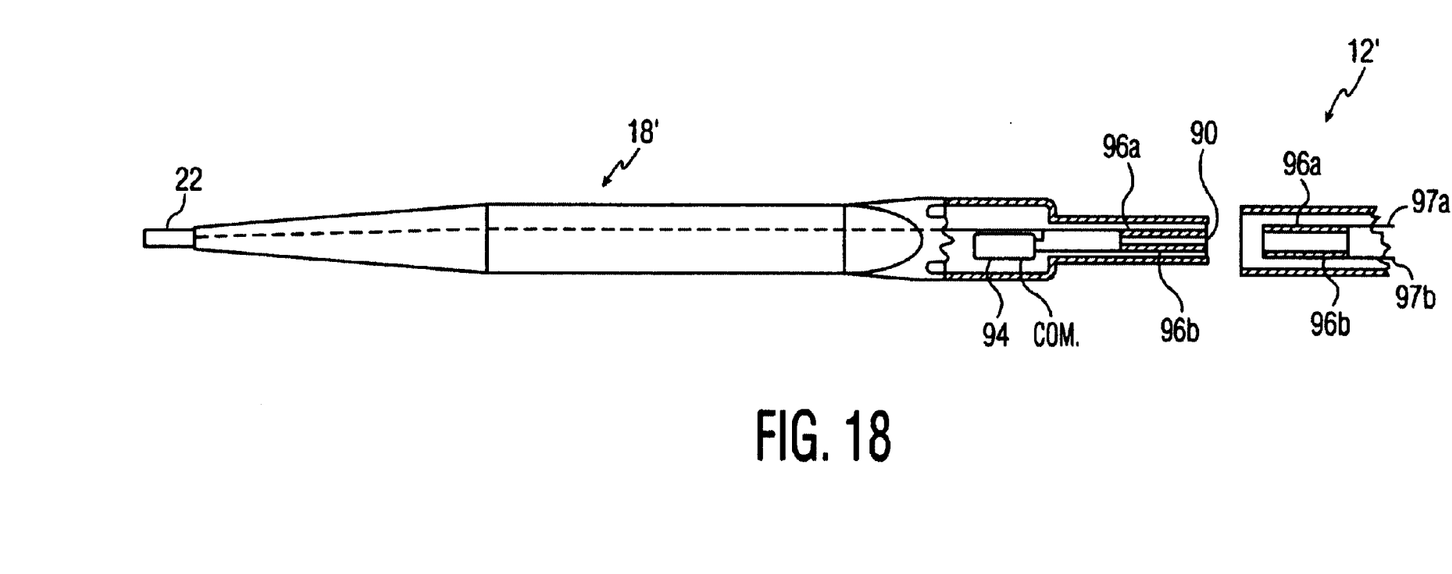
FIG. 18 is top and part sectional view of a modified handpiece incorporating a component.

2. To implement the invention of the copending application, it is very simple to incorporate a suitable impedance or other electrical component which will generate a control signal for the electrosurgical instrument to select operating modes. FIG. 18 illustrates one example, wherein the recessed male connector 90 engages a suitably-sized recessed cylindrical female connector 92 when the two sections are engaged. A component 94 is incorporated in the handpiece section 18'. The connectors in this situation each comprise two contacts 96a and 96b which connect, respectively, to two terminals 97a and 97b in the cable connector section 12'. When the two sections are engaged, the two terminals can access the component 94 as described in this and the parent application to select operating modes, and during actual use, the RF power can be supplied via terminal 97a in the usual way. Where a family of handpieces is provided, then the value of the component would be different for a different family member when a different operating mode is desired.

3. A family of handpiece sections are inexpensively provided each with the same configured end section 40 for engaging a common cable-connector section 12.

4. All electrical parts except for the active electrode end are shielded from accidental contact. Thus, the surgeon or assistant can easily switch electrode ends whenever desired.

5. The handle shape can be chosen for easier pressure control and navigation by the surgeon. The assembled handpiece is lightweight allowing a light touch when applying the electrode to the patient's tissue. The orientation of the electrode can be judged without the surgeon actually viewing the electrode.

6. The low manufacturing cost of the handpiece section allows disposal after each use.

7. Color-coding or otherwise physically distinguishing the different handpiece sections will reduce the chance of physician error as a result of using the wrong electrode.

Note that there are many electrosurgical procedures using all kinds of different electrode than those used as illustrative above, and the above examples were chosen to illustrate that each handpiece section can be dedicated to a particular procedure by incorporating the procedure-specific electrode permanently as part of the handpiece.

It will also be understood that the invention is not limited to the specific connectors shown. Also, different shapes of the housing are also considered within the scope of the invention so long as the shape allows for easy hand holding by the surgeon and easy operation.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. A family of handpieces for an electrosurgical instrument comprising:
    (i) each member of the family comprising:
        (a) a handpiece section comprising a handle having at one end a mounting portion configured to removably engage for mounting and for electrically connecting to a complementary part of a cable-connector section, each handpiece section further comprising an electrical component functioning when activated to generate a unique control signal for the electrosurgical instrument,
        (b) a non-removable electrode permanently connected to the opposite end of the handpiece section;
    (ii) the electrode being differently shaped or sized in each member of the family and the electrical component of each handpiece section in each member of the family having different electrical properties such as to generate a different unique control signal,
    (iii) a common cable-connector section for connection to the instrument, the common cable-connector section having at one end a receiving portion for removably receiving each of the mounting portions of each of the handpiece sections, the cable-connector section further comprising a cable and a connector for connecting to the instrument.

2. A family of handpieces as claimed in claim 1, wherein the cable-connector section comprises a molded electrically-insulating body having on its interior one of a male and female electrical connector, each of the handpiece sections comprising a molded electrically-insulating body serving as the handle and having on its interior the other of the male and female electrical connector, the male and female electrical connectors having complementary shapes for electrical engagement when any of the handpiece section's mounting portions engages the cable-connector section receiving portion.

3. A family of handpieces as claimed in claim 2, wherein each handpiece section's body is differently physically configured or labeled or colored to indicate to a user that the attached non-removable electrode is adapted for a different procedure.

4. A family of handpieces as claimed in claim 2, wherein the non-removable electrode of at least one of the handpiece sections is non-circular-symmetrical and has a predetermined fixed orientation with respect to the handle of said one handpiece section, and the handle of said one handpiece section has a predetermined non-circular-symmetrical physical configuration related to the orientation of the electrode such as to indicate to a user holding the handle the predetermined orientation of the electrode.

5. A family of handpieces as claimed in claim 4, wherein the non-removable electrode of said one handpiece section is planar, and said one handpiece section has a cross section with at least one flat side that is orientated parallel to the plane of the electrode.

6. A family of handpieces as claimed in claim 5, wherein said one handpiece section has a triangular cross section with one of its sides extending parallel to the plane of the electrode.

7. A family of handpieces as claimed in claim 4, wherein the non-removable electrode of said one handpiece section is planar, and said one handpiece section has a cross section with at least one vertex with which the plane of the electrode is orientated in parallel relationship.

8. A family of handpieces as claimed in claim 7, wherein said one handpiece section has a triangular cross section with one of its vertices oriented to the plane of the electrode.

9. A family of handpieces as claimed in claim 2, wherein the handpiece section is free of electrical wires or cables or connectors for connecting to the electrosurgical instrument.

10. A handpiece for an electrosurgical instrument comprising:
  (a) a handpiece section comprising a handle having at one end a mounting portion configured to removably engage for mounting and for electrically connecting to a complementary part of a cable-connector section,
  (b) a non-removable electrode permanently connected to the opposite end of the handle,
  (c) the handpiece section being free of electrical wires or cables or connectors for connecting to the electrosurgical instrument,
  (d) the non-removable electrode being non-circular-symmetrical and having a given fixed orientation,
  (e) the handle having a a triangular cross section related to the orientation of the electrode such as to indicate to a user holding the handle the given orentation of the electrode.

11. An electrosurgical procedure, comprising:
(A) providing an electrosurgical instrument for receiving a common cable-connector section,
(B) providing a family of handpieces for the electrosurgical instrument,
  (a) each member of the family comprising:
    (i) a handpiece section having at one end a mounting portion configured to removably engage for mounting and for electrically connecting to a complementary part of a cable-connector section, the handpiece section further comprising an electrical component functioning when activated to generate a unique control signal for the electrosurgical instrument,
    (ii) an electrode permanently connected to the opposite end of the handpiece section,
  (b) the electrode being differently shaped or sized in each member of the family and the electrical component of each handpiece section in each member of the family having different electrical properties such as to generate a different unique control signal,
  (c) a common cable-connector section connected to the instrument, the common cable-connector section having at one end a receiving portion for removably receiving each of the mounting portions of each of the handpiece sections,
(C) mounting a first member of the family to the cable-connector section,
(D) applying the electrode of the first family member to the patient while activating the instrument to conduct a first part of a procedure controlled by the unique control signal generated by the electrode of the first member,
(E) removing the first member of the family from the cable-connector section and mounting a second member of the family to the cable-connector section,
(F) applying the electrode of the second family member to the patient while activating the instrument to conduct a second part of the procedure controlled by the unique control signal generated by the electrode of the second member, the second part of the procedure being different from the first part.

* * * * *